United States Patent [19]

Bell et al.

[11] 4,359,421

[45] Nov. 16, 1982

[54] PROCESS FOR MAKING EPSILON-CAPROLACTAM

[75] Inventors: Weldon K. Bell, Pennington; Clarence D. Chang, Princeton, both of N.J.

[73] Assignee: Mobil Oil Corporation, New York, N.Y.

[21] Appl. No.: 225,157

[22] Filed: Jan. 15, 1981

[51] Int. Cl.³ .............................................. C07D 201/04
[52] U.S. Cl. .............................................. 260/239.3 A
[58] Field of Search ................................. 260/239.3 A

[56] References Cited

U.S. PATENT DOCUMENTS 3,503,958  3/1970  Landis .......................... 260/239.3 A

*Primary Examiner*—Robert T. Bond
*Attorney, Agent, or Firm*—Charles A. Huggett; Michael G. Gilman; Claude E. Setliff

[57] ABSTRACT

Process for preparing caprolactam from cyclohexanone oxime by passing the oxime, preferably dissolved in a solvent, over a zeolite having a $SiO_2/Al_2O_3$ of at least 12 and a Constraint Index of from 1 to 12.

13 Claims, No Drawings

PROCESS FOR MAKING EPSILON-CAPROLACTAM

BACKGROUND OF THE INVENTION

1. Field of the Invention

The invention relates to the manufacture of caprolactam. More particularly, it relates to the manufacture of lactam by passing cyclohexanone oxime over a zeolite.

2. Discussion of the Prior Art

Manufacture of caprolactam from cyclohexanone oxime is well known. For example, rearrangement of this compound was reported as early as 1900 in Ann. 312, 187 (1900). The patent literature also discloses various reactions that yield caprolactams. For example, U.S. Pat. No. 3,016,375 teaches the rearrangement of cyclohexanone oxime using polyphosphoric acid.

In addition, U.S. Pat. No. 3,000,877 teaches a process for making caprolactams involving a reaction of 6-acetoxycaproic acid or 6-acetoxycaproic acid lactone adducts with aqueous ammonia. U.S. Pat. No. 3,000,878 discloses making them by reacting alkyl-substituted epsilon-caprolactone with aqueous ammonia, U.S. Pat. No. 3,000,879 by heating 6-hydroxycaproamide in water and U.S. Pat. No. 3,000,880 by heating epsilon-caprolactone with aqueous R—$NH_2$, where R is hydrogen or lower alkyl.

In the Journal of Catalysis, 6, 247-253 (1966), P. S. Landis and P. B. Venuto disclose the rearrangement of cyclohexanone oxime over a Y zeolite.

No art is known, however, that teaches conversions to caprolactams using the disclosed zeolites as the catalyst.

SUMMARY OF THE INVENTION

In accordance with this invention, there is provided a process for preparing a caprolactam comprising passing a cyclohexanone oxime over a zeolite having a $SiO_2$ to $Al_2O_3$ of at least 12 and a Constraint Index of 1 to 12.

DESCRIPTION OF SPECIFIC EMBODIMENTS

In conventional manufacture, the rearrangement of cyclohexanone oxime to epsilon-caprolactam is accomplished with high selectivity using sulfuric acid as a homogeneous (liquid phase) catalyst. However, subsequent processing necessitates neutralizing the reaction mixture by addition of excess ammonia and the separation of ammonium sulfate from the end product. The result is the co-production of large amounts of ammonium sulfate, since sulfuric acid is not readily recoverable from the salt for recycle. Vapor phase reaction with a solid acid catalyst offered some improvement, with the elimination of these latter problems. However, previously investigated acid catalysts showed rapid aging generally accompanied by reduced selectivity. The ZSM-5 type catalyst show improved aging and selectivity characteristics.

The crystalline zeolites utilized herein are members of a novel class of zeolitic materials which exhibit unusual properties. Although these zeolites have unusually low alumina contents, i.e. high silica to alumina mole ratios, they are very active even when the silica to alumina mole ratio exceeds 30. The activity is surprising since catalytic activity is generally attributed to framework aluminum atoms and/or cations associated with these aluminum atoms. These zeolites retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. These zeolites, used as catalysts, generally have low coke-forming activity and therefore are conducive to long times on stream between regenerations by burning carbonaceous deposits with oxygen-containing gas such as air.

An important characteristic of the crystal structure of this novel class of zeolites is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves being bonded to the silicon (or aluminum, etc.) atoms at the centers of the tetrahedra.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although zeolites with a silica to alumina mole ratio of at least 12 are useful, it is preferred in some instances to use zeolites having substantially higher silica/alumina ratios, e.g. 1600 and above. In addition, zeolites as otherwise characterized herein but which are substantially free of aluminum, that is zeolites having silica to alumina mole ratios of up to infinity, are found to be useful and even preferable in some instances. Such "high silica" or "highly siliceous" zeolites are intended to be included within this description. Also to be included within this definition are substantially pure silica analogs of the useful zeolites described herein, that is to say those zeolites having no measurable amount of aluminum (silica to alumina mole ratio of infinity) but which otherwise embody the characteristics disclosed.

The novel class of zeolites, after activation, acquire an intracrystalline sorption capacity for normal hexane which is greater than that for water, i.e. they exhibit "hydrophobic" properties. This hydrophobic character can be used to advantage in some applications.

The novel class of zeolites useful herein have an effective pore size such as to freely sorb normal hexane. In addition, the structure must provide constrained access to larger molecules. It is sometimes possible to judge from a known crystal structure whether such constrained access exists. For example, if the only pore windows in a crystal are formed by 8-membered rings of silicon and aluminum atoms, then access by molecules of larger cross-section than normal hexane is excluded and the zeolite is not of the desired type. Windows of 10-membered rings are preferred, although in some instances excessive puckering of the rings or pore blockage may render these zeolites ineffective.

Although 12-membered rings in theory would not offer sufficient constraint to produce advantageous conversions, it is noted that the puckered 12-ring structure of TMA offretite does show some constrained access. Other 12-ring structures may exist which may be operative for other reasons and, therefore, it is not the present intention to entirely judge the usefulness of a particular zeolite solely from theoretical structural considerations.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

While the above experimental procedure will enable one to achieve the desired overall conversion of 10 to 60% for most zeolite samples and represents preferred conditions, it may occasionally be necessary to use somewhat more severe conditions for samples of very low activity, such as those having an exceptionally high silica to alumina mole ratio. In those instances, a temperature of up to about 540° C. and a liquid hourly space velocity of less than one, such as 0.1 or less, can be employed in order to achieve a minimum total conversion of about 10%.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of 1 to 12. Constraint Index (CI) values for some typical materials are:

TABLE 1

|  | C.I. |
|---|---|
| ZSM-4 | 0.5 |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 0.6 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined novel class of highly siliceous zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than an exclusive value. That is, a crystalline zeolite when identified by any combination of conditions within the testing definition set forth herein as having a Constraint Index in the range of 1 to 12 is intended to be included in the instant novel zeolite definition whether or not the same identical zeolite, when tested under other of the defined conditions, may give a Constraint Index value outside of the range of 1 to 12.

The novel class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. Nos. 3,702,886 and Re. 29,948. The entire descriptions contained within those patents, particularly the X-ray diffraction pattern of therein disclosed ZSM-5, are incorporated herein by reference.

ZSM-11 is described in U.S. Pat. No. 3,709,979. That description, and in particular the X-ray diffraction pattern of said ZSM-11, is incorporated herein by reference.

ZSM-12 is described in U.S. Pat. No. 3,832,449. That description, and in particular the X-ray diffraction pattern disclosed therein, is incorporated herein by reference.

ZSM-23 is described in U.S. Pat. No. 4,076,842. The entire content thereof, particularly the specification of the X-ray diffraction pattern of the disclosed zeolite, is incorporated herein by reference.

ZSM-35 is described in U.S. Pat. No. 4,016,245. The description of that zeolite, and particularly the X-ray diffraction pattern thereof, is incorporated herein by reference.

ZSM-38 is more particularly described in U.S. Pat. No. 4,046,859. The description of that zeolite, and particularly the specified X-ray diffraction pattern thereof, is incorporated herein by reference.

ZSM-48 can be identified, in terms of moles of anhydrous oxides per 100 moles of silica, as follows:

(0–15)RN:(0–1.5)M$_{2/n}$O:(0–2)Al$_2$O$_3$:(100)SiO$_2$ wherein:

M is at least one cation having a valence n; and

RN is a $C_1$–$C_{20}$ organic compound having at least one amine functional group of $pK_a \geq 7$.

It is recognized that, particularly when the composition contains tetrahedral, framework aluminum, a fraction of the amine functional groups may be protonated. The doubly protonated form, in conventional notation, would be $(RNH)_2O$ and is equivalent in stoichiometry to $2RN + H_2O$.

The characteristic X-ray diffraction pattern of the synthetic zeolite ZSM-48 has the following significant lines:

TABLE 2

| Characteristic Lines of ZMS-48 | |
|---|---|
| d (Angstroms) | Relative Intensity |
| 11.9 | W-S |
| 10.2 | W |
| 7.2 | W |
| 5.9 | W |
| 4.2 | VS |
| 3.9 | VS |
| 3.6 | W |
| 2.85 | W |

These values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, $100\ I/I_o$, where $I_o$ is the intensity of the strongest line or peak, and d (obs.), the interplanar spacing in A, corresponding to the recorded lines, were calculated. In the foregoing table the relative intensities are given in terms of the symbols W=weak, VS=very strong and W-S=weak-to-strong. Ion exchange of the sodium with cations reveals substantially the same pattern with some minor shifts in interplanar spacing and variation in relative intensity. Other minor variations can occur depending on the silicon to aluminum ratio of the particular sample, as well as if it has been subjected to thermal treatment.

The ZSM-48 can be prepared from a reaction mixture containing a source of silica, water, RN, an alkali metal oxide (e.g. sodium) and optionally alumina. The reaction mixture should have a composition, in terms of mole ratios of oxides, falling within the following ranges:

TABLE 3

| REACTANTS | BROAD | PREFERRED |
|---|---|---|
| $Al_2O_3/SiO_2 =$ | 0 to 0.02 | 0 to 0.01 |
| $Na/SiO_2 =$ | 0 to 2 | 0.1 to 1.0 |
| $RN/SiO_2 =$ | 0.01 to 2.0 | 0.05 to 1.0 |
| $OH^-/SiO_2 =$ | 0 to 0.25 | 0 to 0.1 |
| $H_2O/SiO_2 =$ | 10 to 100 | 20 to 70 |
| $H^+$ (added)/$SiO_2 =$ | 0 to 0.2 | 0 to 0.05 | wherein RN is a $C_1$–$C_{20}$ organic compound having amine functional group of $pK_a \geq 7$. The mixture is maintained at 80°–250° C. until crystals of the material are formed. $H^+$(added) is moles acid added in excess of the moles of hydroxide added. In calculating $H^+$(added) and OH values, the term acid ($H^+$) includes both hydronium ion, whether free or coordinated, and aluminum. Thus aluminum sulfate, for example, would be considered a mixture of aluminum oxide, sulfuric acid, and water. An amine hydrochloride would be a mixture of amine and HCl. In preparing the highly siliceous form of ZSM-48 no alumina is added. Thus, the only aluminum present occurs as an impurity in the reactants.

Preferably, crystallization is carried out under pressure in an autoclave or static bomb reactor at 80° C. to 250° C. Thereafter, the crystals are separated from the liquid and recovered. The composition can be prepared utilizing materials which supply the appropriate oxide. Such compositions include sodium silicate, silica hydrosol, silica gel, silicic acid, RN, sodium hydroxide, sodium chloride, aluminum sulfate, sodium aluminate, aluminum oxide, or aluminum itself. RN is a $C_1$–$C_{20}$ organic compound containing at least one amine functional group of $pK_a \geq 7$, as defined above, and includes such compounds as $C_3$–$C_{18}$ primary, secondary, and tertiary amines, cyclic amine (such as piperidine, pyrrolidine and piperazine), and polyamines such as $NH_2$—$C_nH_{2n}$—$NH_2$ wherein n is 4–12.

The original cations can be subsequently replaced, at least in part, by for example, calcination, impregnation and/or ion exchange with another cation. Thus, the original cations are exchanged into a hydrogen or hydrogen ion precursor form or a form in which the original cation has been replaced by a metal of Groups II through VIII of the Periodic Table, including specifically Group II, Group VIB, e.g., chromium and molybdenum, and VIII. Thus, for example, it is contemplated to exchange the original cations with ammonium ions or with hydronium ions. Catalytically active forms of these would include, in particular, hydrogen, rare earth metals, aluminum, manganese and other metals of Groups II, VIB and VIII of the Periodic Table.

It is to be understood that by incorporating by reference the foregoing patents to describe examples of specific members of the novel class with greater particularity, it is intended that identification of the therein disclosed crystalline zeolites be resolved on the basis of their respective X-ray diffraction patterns. As discussed above, the present invention contemplates utilization of such catalysts wherein the mole ratio of silica to alumina is essentially unbounded. The incorporation of the identified patents should therefore not be construed as limiting the disclosed crystalline zeolites to those having the specific silica-alumina mole ratios discussed therein, it now being known that such zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

The preferred crystalline zeolites for utilization herein include ZSM-5, ZSM-11, ZSM-12, ZSM-23, ZSM-35, ZSM-38, and ZSM-48, with ZSM-5 being particularly preferred.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired for several reasons. When hydrocarbon products or by-products are catalytically formed, for example, such zeolites tend to maximize the production of gasoline boiling range hydrocarbon products. Therefore, the preferred zeolites useful with respect to this invention are those having a Constraint Index as defined above of about 1 to about 12, a silica to alumina mole ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on Page 19 of the article ZEOLITE STRUCTURE by W. M. Meier. This paper, the entire contents of which are incorporated herein by reference, is included in PROCEEDINGS OF THE CONFERENCE ON MOLECULAR SIEVES, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

TABLE 4

| | Void Volume | Framework Density |
|---|---|---|
| Ferrierite | 0.2 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing a particularly desired chemical conversion process, it may be useful to incorporate the above-described crystalline zeolite with a matrix comprising another material resistant to the temperature and other conditions employed in the process. Such matrix material is useful as a binder and imparts greater resistance to the catalyst for the severe temperature, pressure and reactant feed stream velocity conditions encountered in many cracking processes.

Useful matrix materials include both synthetic and naturally occurring substances, as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

Conversion of the cyclohexanone oxime in the presence of the catalyst described herein generally takes place at from about 0.01 to about 10 LHSV, about 300° to about 1000° F. and at about 0.5 to about 500 psig. It is to be understood that any suitable reactor can be used.

The useful solvents include benzene, xylene, toluene and the like. In general, any non-reactive solvent that can be easily removed from the product can be used. The amount of solvent does not appear to be critical, and the solution thereof with oxime will range from about 1 weight percent to about 50 weight percent of solvent, with complementary amounts of oxime.

Having described the invention in broad terms, the following will provide a specific illustration.

EXAMPLE 1

The HZSM-5 used in Examples 3 and 4 was made as follows:

A sodium silicate solution was prepared by mixing 16 parts water and 27.7 parts of sodium silicate (28.7 wt % $SiO_2$, 8.9 wt % $Na_2O$, 62.4% $H_2O$) followed by addition of 0.08 parts of Daxad 27 (W. R. Grace Chemical Division). The solution was cooled to approximately 15° C.

An acid solution was prepared by adding 1 part of aluminum sulfate (17.2 wt % $Al_2O_3$) to 16.4 parts of water, followed by 2.4 parts of sulfuric acid (93 wt % $H_2SO_4$) and 1.2 parts of NaCl.

These solutions were mixed in an agitated vessel while 3.9 parts of NaCl were added. The gel molar ratios expressed as oxides are the following:

$SiO_2/Al_2O_3 = 78.4$ $Na_2O/Al_2O_3 = 49.9$

An organic solution was prepared by adding 1.6 parts of n-propyl bromide and 3.2 parts of methyl ethyl ketone to 1.9 parts of tri-n-propylamine.

After the gel was heated to about 95° C., agitation was reduced and the organic solution was added above the gel. This mixture was held at about 95°-110° C. for 14 hours, then severe agitation was resumed. When approximately 65% of the gel was crystallized, the temperature was increased to 150°-160° C. and held there until crystallization was complete. Unreacted organics were removed by flashing and the remaining contents cooled.

The zeolite slurry product was diluted with 4-5 parts of water per part of slurry and 0.0002 parts of flocculent (Rohm & Haas Primafloc C-7) per part of slurry, allowed to settle and supernatant liquid was drawn off. The settled solids were reslurried to the original volume of the preceding step with water and 0.00005 parts of flocculant per part slurry. After settling, the aqueous phase was decanted. This procedure was repeated until the sodium level of the zeolite was less than 1.0 wt %. The washed zeolite was then filtered, dried.

The dried zeolite was then mixed with alumina and water. It was then extruded into 1/16" pellets and dried. The extruded material contained 65 parts ZSM-5 per 35 parts alumina.

The dried extrudate was calcined for three hours at 538° C. in flowing nitrogen. After cooling, the extrudate was contacted with an ammonium nitrate exchange solution (about 0.08 lb $NH_4NO_3$/lb extrudate) for one hour at ambient temperature. This exchange was then repeated until the sodium level was less than 0.05 wt %. The extrudate was washed, dried and calcined in a flowing gas mixture (approximately 10% air-90% nitrogen) at 538° C. for six hours.

EXAMPLE 2

This Example illustrates ZSM-5 containing other metal cations.

A sodium silicate solution was prepared by mixing 16.7 parts of water and 28.9 parts of sodium silicate (28.7 wt % $SiO_2$, 8.9 wt % $Na_2O$, 62.4% $H_2O$) followed by addition of 0.08 parts of Daxad 27 (W. R. Grace Chemical Division).

An acid solution was prepared by adding 1 part of aluminum sulfate (17.2 wt % $Al_2O_3$) to 17.1 parts of water followed by 2.4 parts of sulfuric acid (95 wt % $H_2SO_4$) and 3.4 parts of NaCl.

These solutions were mixed in an agitated vessel while 2.0 parts of NaCl were added.

An organic solution was prepared by adding 1.7 parts of n-propylbromide and 3.2 parts methyl ethyl ketone to 1.9 parts of tri-n-propylamine.

Agitation of the gel was stopped and the organic solution was added above the gel. The vessel was sealed and heated to ~105° C. without agitation and held there for 14-15 hours to prereact the organics. At the end of the prereaction period, the agitation was commenced to start the initial crystallization period. After about 75-80 hours the temperature was raised to 160° C. and held there for about three hours to complete crystallization. The excess or unreacted organics were flashed off and the contents of the autoclave were cooled and discharged. The produce was analyzed by x-ray diffraction and shown to be 100% crystallinity ZSM-5 based upon a standard sample.

After thorough washing and drying at ~120° C., the zeolite was then mixed with alumina and water. It was then extruded into 1/16" pellets and dried. The extruded material contained 65 parts ZSM-5 per 35 parts alumina.

The dried extrudate was calcined for three hours at 538° C. in flowing nitrogen. After cooling, the extrudate was contacted with an ammonium nitrate exchange solution (about 0.4 lb $NH_4NO_3$/lb extrudate) for one hour at ambient temperature. This exchange was repeated until the sodium level was less than 0.05 wt %. The extrudate was then contacted with a nickel nitrate exchange solution (about 0.7 lb of $Ni(NO_3)_2.6H_2O$/lb extrudate) for 4 hours at 89°-90° C. The extrudate was then washed, dried and calcined in flowing air at 538° C. for three hours.

EXAMPLE 3

An 8% solution of cyclohexanone oxime in benzene was prepared. A bed of the HZSM-5 catalyst of Example 1 was placed in a suitable reactor, and the 8% solution of oxime in benzene was fed over same at 1.7 LHSV (liquid hourly space velocity), at a temperature of 832° F. (350° C.) and at a pressure of 1 atmosphere. The conversion at 832° F. was nearly quantitative for periods of up to about 15 hours.

It has been shown that, at 832° F., conversion rapidly drops off after 15 hours on stream and that conversion with the same catalyst returns to maximum value following air regeneration. There appears to be no limitation on the number of times the catalyst can be regenerated.

EXAMPLE 4

A 14.4% solution of cyclohexanone oxime in benzene was prepared and fed over a bed of HZSM-5 catalyst at 1.7 LHSV (liquid hourly space velocity), at a temperature of 832° F. (350° C.), and at a pressure of 1 atmosphere. The HZSM-5 catalyst of Example 1 was crushed and charged to the reactor.

It was shown that at 832° F., that conversion began to rapidly drop off after about 15 hours on stream and that conversion of cyclohexanone oxime had dropped to about 40% conversion at about 21 hours on stream.

EXAMPLES 5 AND 6

Similar results were obtained using HZSM-11 and HZSM-23 zeolite catalysts. The HZSM-11 and HZSM-23 zeolites contained, respectively, $SiO_2$ to $Al_2O_3$ ratios of 72 and 112. Calcined zeolite powders were combined with a ½ portion by weight of calcined alpha alumina powder, pelleted and crushed. Feed solutions in benzene were prepared and contained, respectively, 13.7% and 14.7% by weight cyclohexanone oxime. As in the previous examples, aging experiments were conducted in a tubular reactor at 832° F. (350° C.), at a LHSV of 1.7, and at 1 atmosphere. Cyclohexanone oxime conversion behavoirs with time on stream paralleled those of the HZSM-5 catalyst tested in Example 4. For the case of the HZSM-11 catalyst, conversion dropped to about 40% after about 19 hours on stream. For the HZSM-23 catalyst, conversion dropped to about 40% after about 18 hours on stream.

EXAMPLE 7

In testing similar to that of Examples 3 through 6 a REY (rare earth exchanged Y zeolite) catalyst showed much poorer performance in the tubular reactor experiment. A benzene solution containing 14.5% cyclohexanone oxime was fed at a LHSV of 1.7, a temperature of 832° F. (350° C.), and at a pressure of 1 atmosphere over a catalyst bed of crushed pellets. This REY catalyst was pelleted from a mixture of the calcined powders of one part REY zeolite ($ReO_2$-17%, $Al_2O_3$-19%, $SiO_2$-62%, NaO-~2%) and a ½ part by weight alpha alumina. Initially essentially complete conversion of the oxime was observed. Within about 5 hours, conversion of oxime had fallen below 40 wt. %.

EXAMPLE 8

In a test similar to the one used in Examples 3–7, a Ni containing HZSM-5 catalyst showed behavoir similar to that of the HZSM-5 family of catalysts in the tubular reactor test. The catalyst tested is described in Example 2.

A benzene solution of 14.5% cyclohexanone oxime was fed over this catalyst at LHSV 1.7, at a temperature of 832° F. (350° C.), and a pressure of 1 atmosphere. Like the case of the HZSM-5 catalyst tested in Example 4, essentially complete oxime conversion was initially observed, conversion began to rapidly drop off after about 15 hours, and conversion had dropped below 40% after about 21 hours of operation.

EXAMPLE 9

A palladium-zinc impregnated HZSM-5 containing catalyst, like the previous ZSM-5 examples, showed performance superior to the REY catalyst example. An ammonium exchanged ZSM-5 was calcined, contacted with a solution of 6 grams of zinc nitrate hexahydrate per 25 grams of calcined zeolite, dried, and calcined. This material was then contacted with a solution of 0.62 grams palladium tetrammine chloride per 25 grams of the calcined zinc-containing zeolite, dried, and calcined. Analysis of the doubly impregnated zeolite indicated 0.9% palladium and 4.5% zinc by weight. This zeolite component was combined with alumina powder in the weight ratio 35 parts alumina to 65 parts zeolite, pelleted, and crushed.

In the tubular reactor test a benzene solution containing 14.6 wt. % cyclohexanone oxime was charged at a LHSV of 1.7 per hour to the catalyst maintained at 350° C. It is estimated that the initially essentially complete conversion began to drop rapidly after about 10 hours. Conversions below 40% by weight were noted after about 17 hours. (After 15.9 and 19.3 hours of operation the observed conversions were 58.2 and 27.0 wt. %, respectively).

We claim:

1. A process for manufacturing epsilon-caprolactam comprising passing cyclohexanone oxime over a zeolite having a silica to alumina ratio of at least 12 and a Constraint Index of 1 to 12.

2. The process of claim 1 wherein said zeolite is ZSM-5.

3. The process of claim 1 wherein said zeolite is ZSM-11.

4. The process of claim 1 wherein said zeolite is ZSM-23.

5. The process of claim 2 wherein said zeolite is HZSM-5.

6. The process of claim 3 wherein said zeolite is HZSM-11.

7. The process of claim 4 wherein said zeolite is HZSM-23.

8. The process of claim 1 wherein the reaction is run at a LHSV of from about 0.01 to about 10.

9. The process of claim 1 wherein the reaction is run at a temperature of from about 300° F. to about 1000° F.

10. The process of claim 1 wherein the reaction is run at a pressure of from 0.5 to about 500 psig.

11. The process of claim 1 wherein the original cations are replaced, at least in part, with hydrogen, a rare earth metal or mixtures of rare earth metals, aluminum, manganese, Group II, Group VIB or Group VIII metals of the Periodic Chart, or mixtures thereof.

12. The process of claim 2 wherein said zeolite contains the nickel cation.

13. The process of claim 2 wherein said zeolite contains the palladium and zinc cations.

* * * * *